United States Patent [19]

Lam et al.

[11] Patent Number: 5,158,938
[45] Date of Patent: Oct. 27, 1992

[54] REBECCAMYCIN

[75] Inventors: Kin S. Lam, Cheshire; Daniel R. Schroeder, Higganum; Jacqueline Mattei, Branford; James A. Matson; Salvatore Forenza, both of Chesire, all of Conn.

[73] Assignee: Bristol-Myers Squibb Company, New York, N.Y.

[21] Appl. No.: 764,116

[22] Filed: Sep. 23, 1991

Related U.S. Application Data

[63] Continuation of Ser. No. 488,915, Mar. 6, 1990, abandoned.

[51] Int. Cl.$^5$ .................. C07D 273/00; A61K 31/00
[52] U.S. Cl. ........................... 514/42; 514/43; 435/85; 435/87; 536/22; 536/23; 536/24
[58] Field of Search ............... 536/23, 24; 514/42, 514/43; 435/85, 87

[56] References Cited

U.S. PATENT DOCUMENTS

| 4,487,925 | 12/1984 | Nettleton, Jr. et al. | 536/24 |
| 4,524,145 | 6/1985 | Matson | 536/24 |
| 4,552,842 | 11/1985 | Nettleton, Jr. et al. | 536/24 |
| 4,567,143 | 1/1986 | Matson | 536/24 |
| 4,785,085 | 11/1988 | Kaneko et al. | 536/24 |
| 4,808,613 | 2/1989 | Kaneko et al. | 536/24 |
| 5,015,578 | 5/1991 | Schroeder et al. | 536/22 |
| 5,073,633 | 12/1991 | Schroeder et al. | 536/22 |

Primary Examiner—Johnnie R. Brown
Assistant Examiner—J. Oliver Wilson
Attorney, Agent, or Firm—Michelle A. Cepeda-Kaye

[57] ABSTRACT

Addition of bromine to the culture medium during fermentation of a rebeccamycin-producing strain of Saccharothrix aerocolonigenes results in production of a new rebeccamycin derivative having advantageous antineoplastic properties.

5 Claims, 5 Drawing Sheets

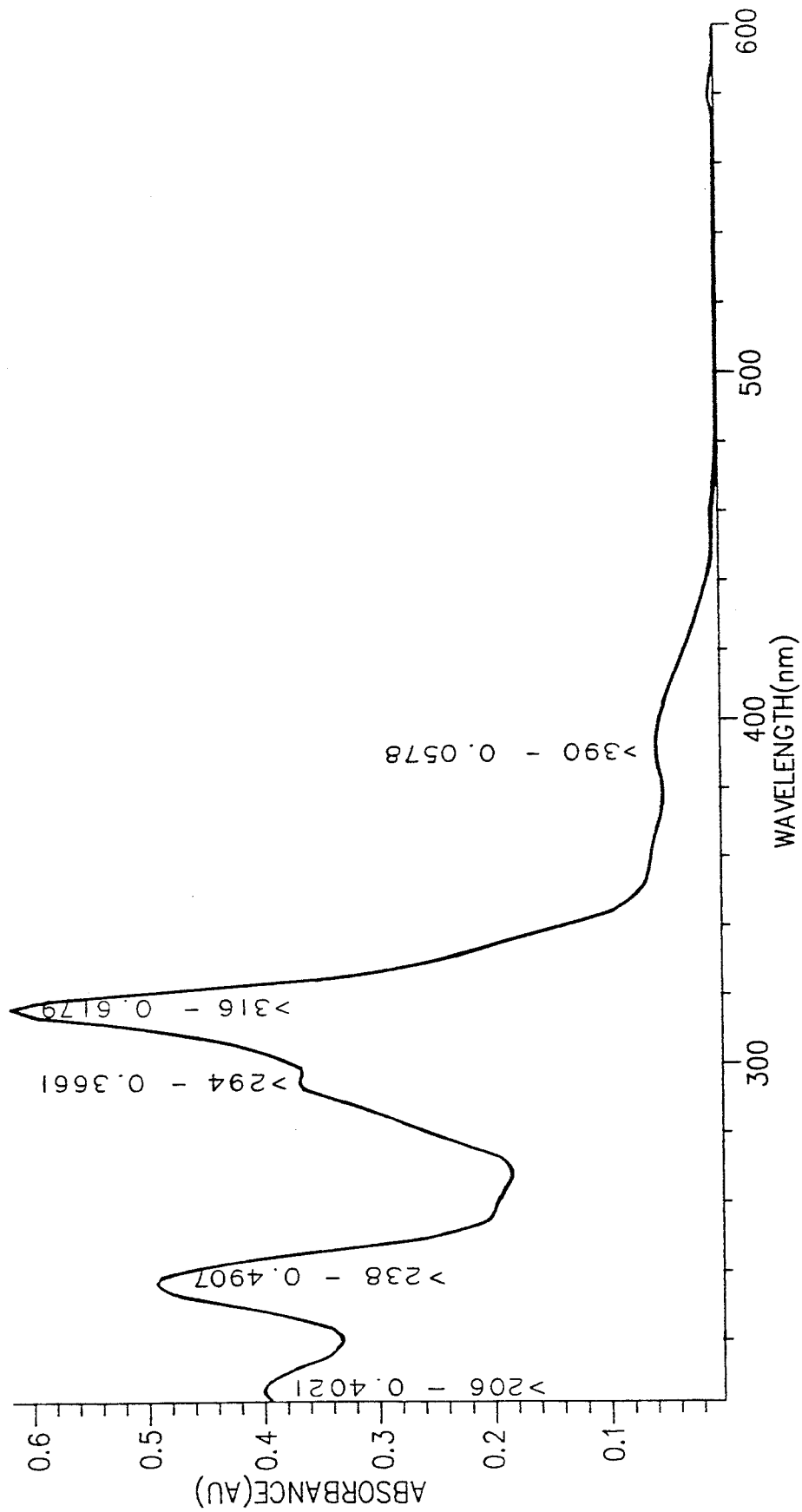

REBECCAMYCIN

This application is a continuation of application Ser. No. 07/488,915, filed Mar. 6, 1990, now abandoned.

BACKGROUND OF THE INVENTION

1. Field of the Invention

This invention relates to a novel analog of rebeccamycin which possesses antineoplastic properties.

2. Background Art

U.S. Pat. Nos. 4,487,925 and 4,552,842 disclose the anti-tumor agent designated rebeccamycin, and the 5'-methyl and 5',2',3'',6''-tetraacetate derivatives thereof, and a process for producing the same agent by cultivating a rebeccamycin-producing strain of *Nocardia aerocolonigenes*, preferably *Nocardia aerocolonigenes* ATCC 39243, or a rebeccamycin-producing mutant thereof in an aqueous nutrient medium containing assimilable sources of carbon and nitrogen under submerged aerobic conditions until a substantial amount of rebeccamycin is produced. Recently *Nocardia aerocolonigenes* ATCC 39243 was reclassified as *Saccharothrix aerocolonigenes* ATCC 39243 (Bush, et al., *J. Antibiotics* 40: 668-678, 1987).

SUMMARY OF THE INVENTION

The present invention provides a new analog of the antitumor agent designated rebeccamycin (Formula I)

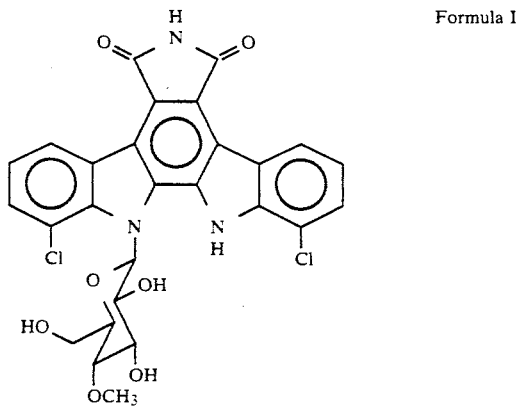

Formula I

More specifically, there is provided the rebeccamycin analog having the Formula II below,

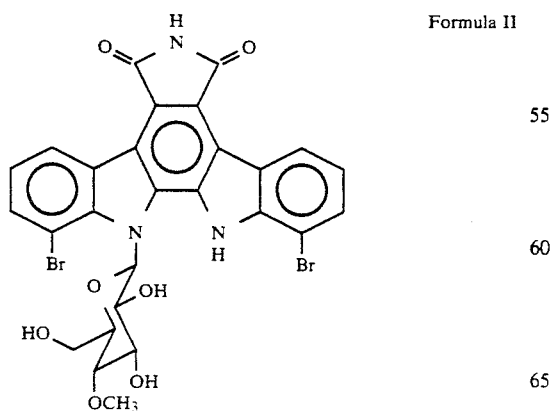

Formula II as well as pharmaceutically acceptable acid addition salts of such analog.

The rebeccamycin analog of Formula II, is produced by cultivating a rebeccamycin-producing strain of Saccharothrix aerocolonigenes in a chlorine-deficient, bromine-enriched media.

DESCRIPTION OF THE DRAWINGS

FIG. 5 shows the UV spectrum of the compound of Formula II.

DETAILED DESCRIPTION OF THE INVENTION

Figure 1:
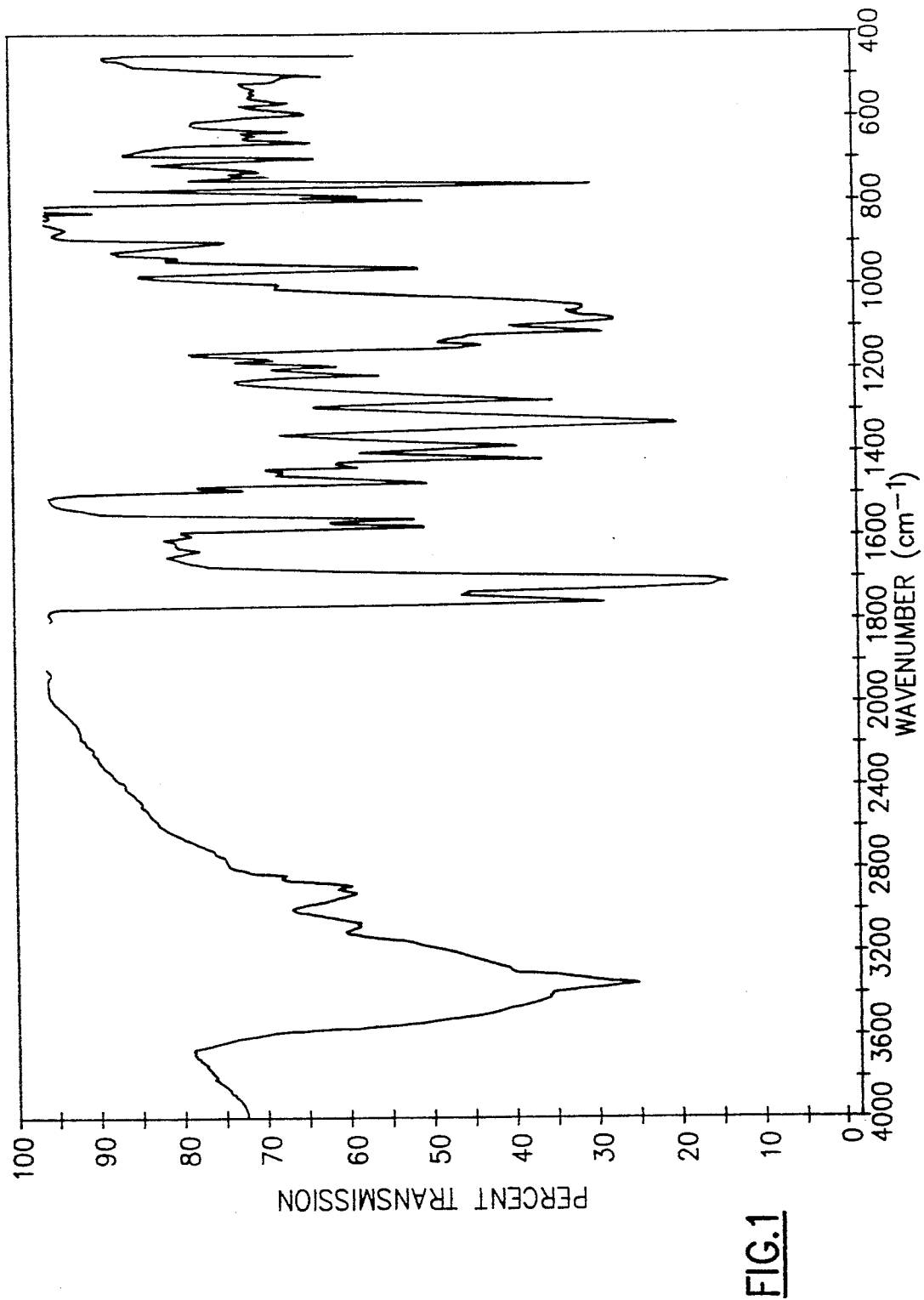
FIG. 1 shows the IR spectrum of the compound of Formula II.
Figure 2:
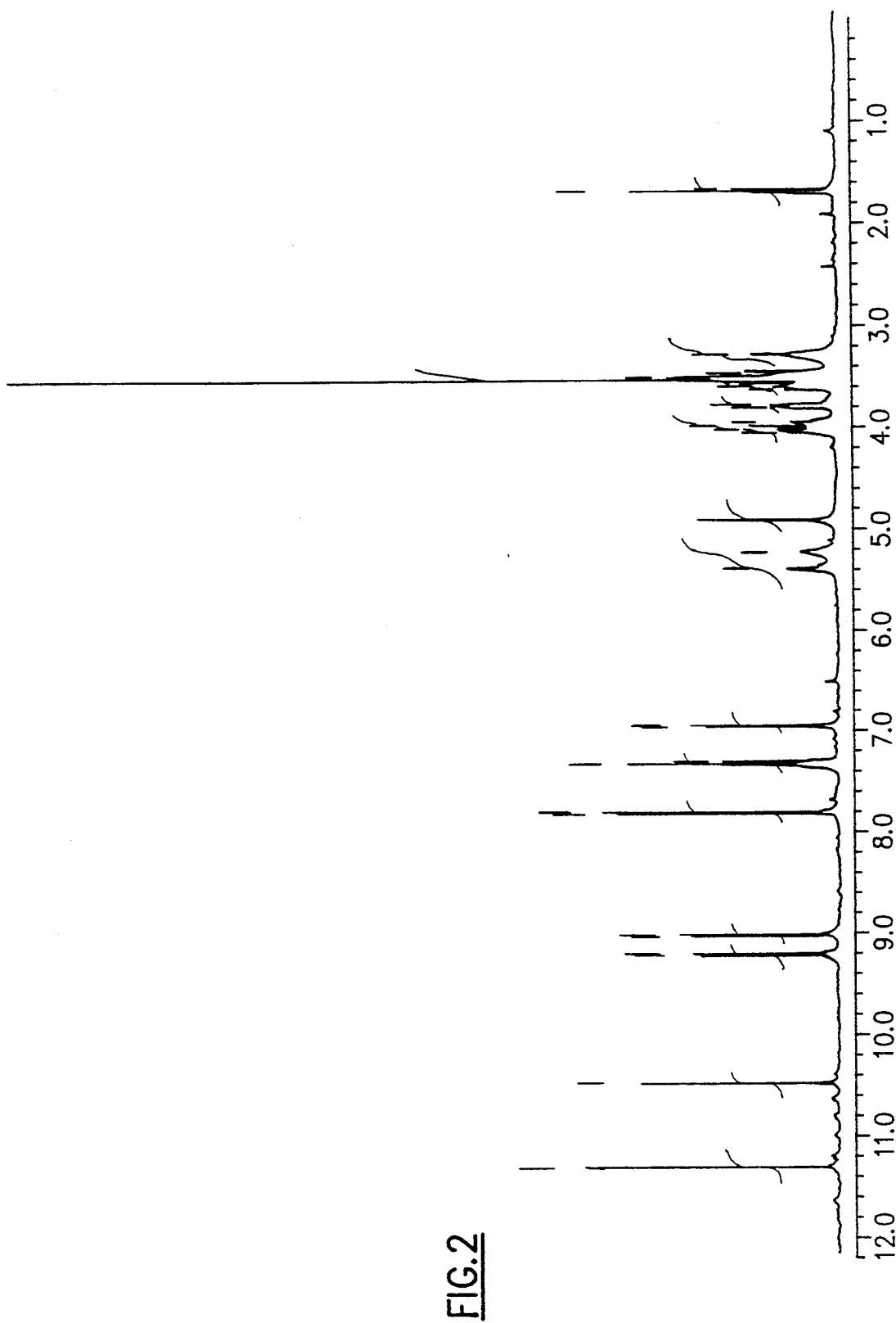
FIG. 2 shows the $^1$H-NMR spectrum of the compound of Formula II.
Figure 3:
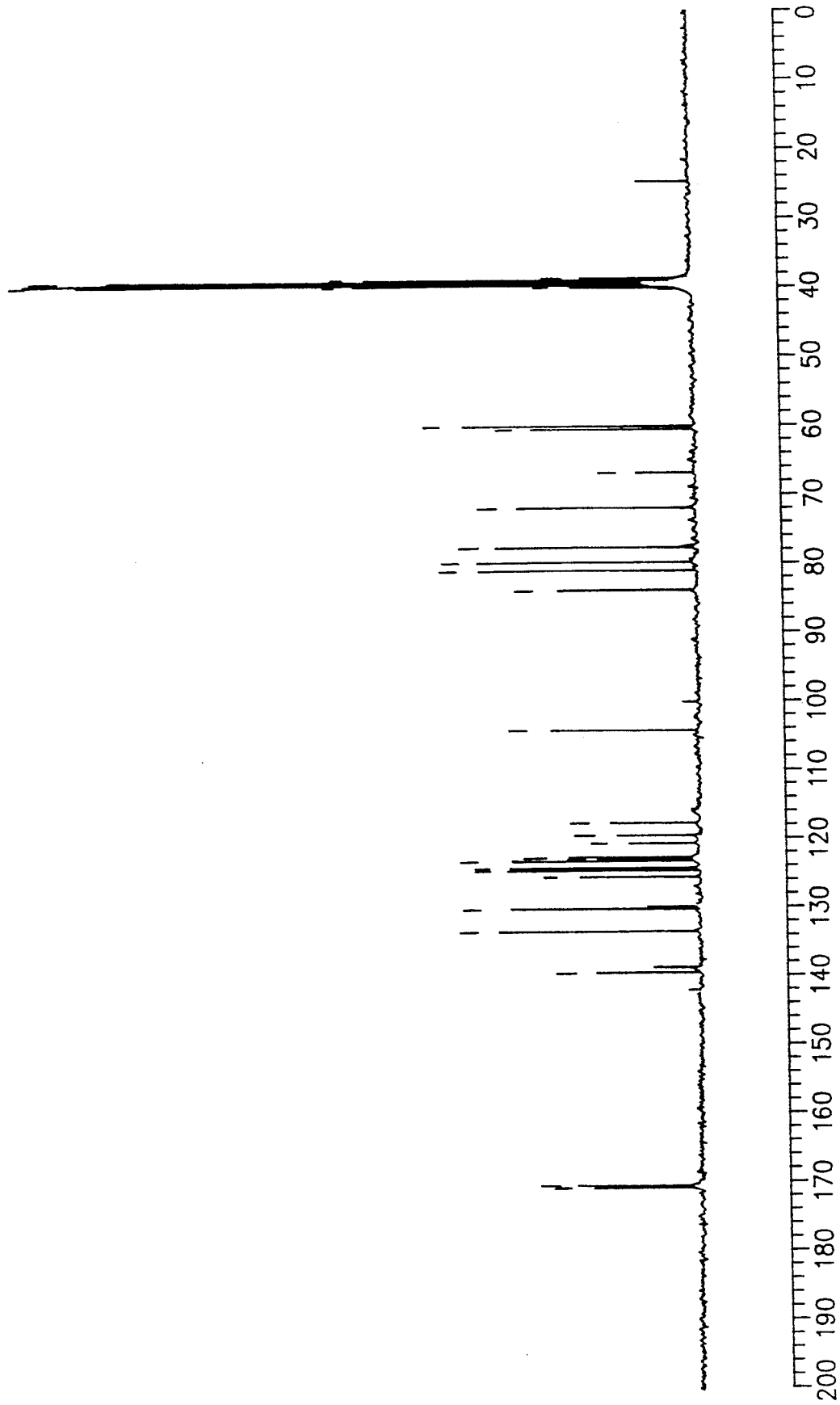
FIG. 3 shows the $^{13}$C-NMR spectrum of the compound of Formula II.
Figure 4:
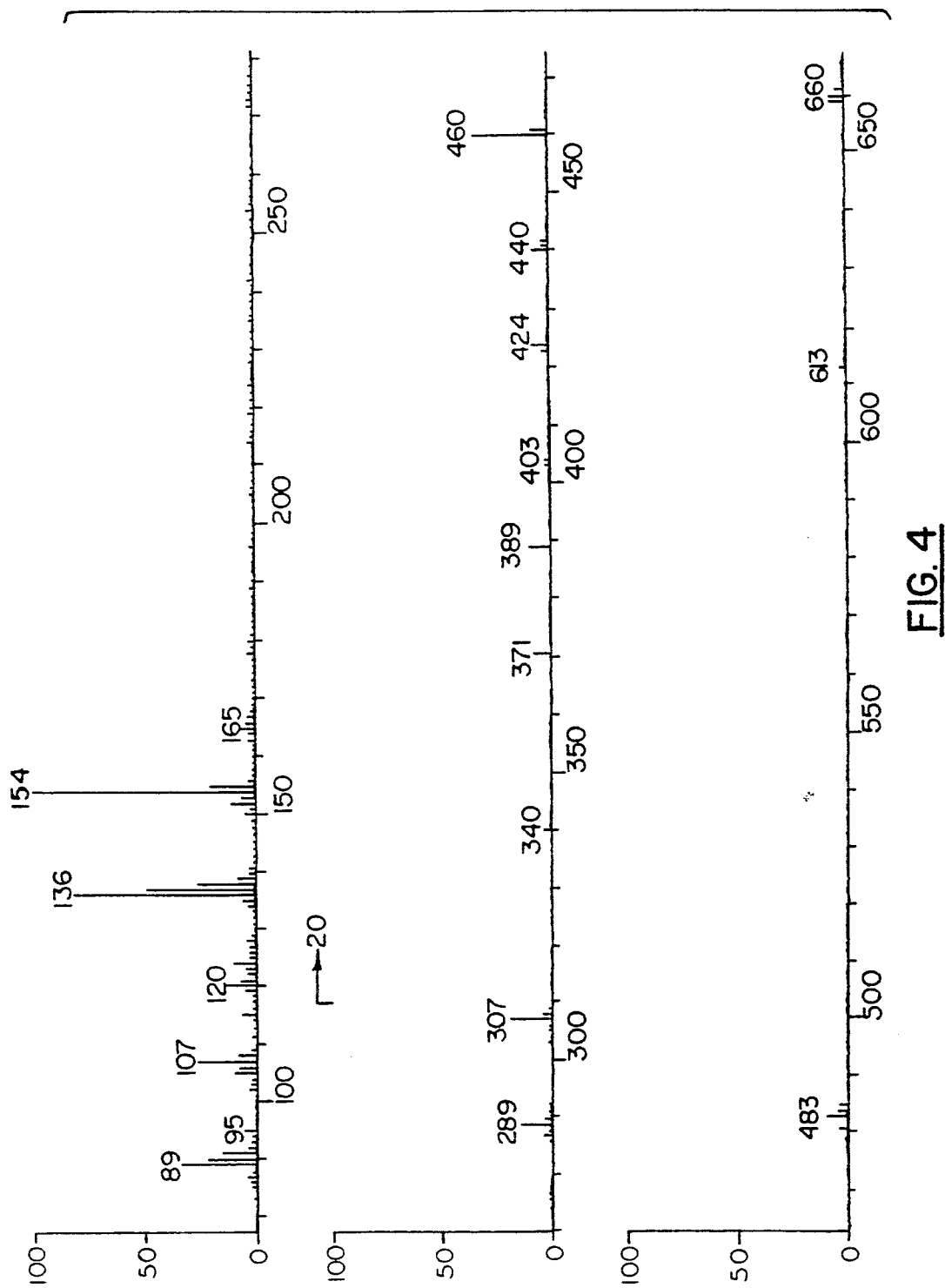
FIG. 4 shows the mass spectrum of the compound of Formula II.

U.S. Pat. Nos. 4,487,925 and 4,552,842 disclose the production and isolation of the antitumor agent designated rebeccamycin (Formula I)

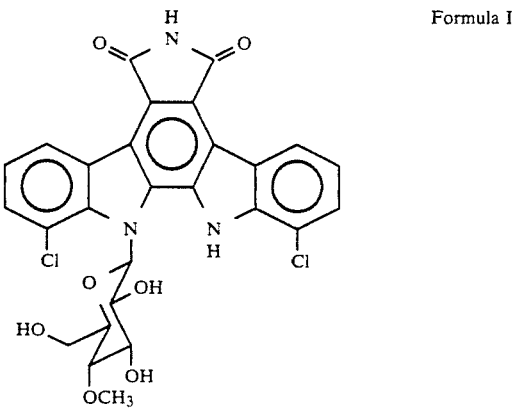

Formula I

The above-mentioned rebeccamycin compound is the principal component of the fermentation of the rebeccamycin producing strain of *Saccharothrix aerocolonigenes*.

It has now been found according to the present invention that the fermentation procedure disclosed in U.S. Pat. Nos. 4,487,925 and 4,552,842 can be carried out in a chlorine-deficient, bromine-enriched media to produce a new analog of rebeccamycin having valuable antineoplastic properties. The rebeccamycin analog of the present invention has the Formula II below:

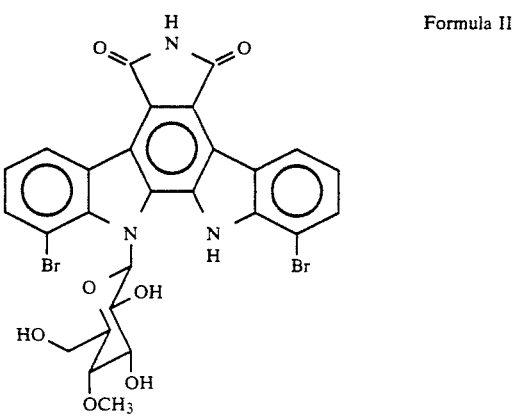

Formula II

In the present process the rebeccamycin fermentation process of U.S. Pat. Nos. 4,487,925 and 4,552,842 is carried out in a chlorine deficient, bromine-enriched media. The bromine is this incorporated into the rebeccamycin ring system replacing the chlorine during fermentation to form a new derivative. A more extensive description of the process is given below and in the illustrative examples which follow.

Preparation of the Antibiotics

The compound of Formula II is produced by fermentation of the strain *Saccharothrix aerocolonigenes* in an aqueous nutrient medium containing bromide ion and preferably with no addition of chloride ion. The preferred producing organism is a novel strain of *Saccharothrix aerocolonigenes* previously designated as *Nocardia aerocolonigenes* strain C38,383-RK2 (ATCC 39243) in U.S. Pat. No. 4,487,925. Recently, this strain was reclassified as *Saccharothrix aerocolonigenes* (Bush et al., *J. Antibiotics* 40:668-678, 1987) and is designated herein as *Saccharothrix aerocolonigenes* strain C38,383-RK2 (ATCC 39243). This strain was isolated from a soil sample collected in Panama. A biologically pure culture of strain C38,383-RK2 has been deposited with the American Type Culture Collection, Rockville, Maryland, and added to their permanent collection of microorganisms as ATCC 39243. This culture, designated as C38,383-RK2, is also maintained as a dormant culture in lyophile tubes and cryogenic vials in the Bristol-Myers Squibb Co. Pharmaceutical Research and Development Division Culture Collection, 5 Research Parkway, Wallingford, Connecticut 06492.

The taxonomic studies on strain C38,383-RK2 (ATCC 39243) have been described in detail in U.S. Pat. No. 4,487,925 and in J. Antibiotics 40:668-678, 1987. The strain has been classified as a novel strain of *Saccharothrix aerocolonigenes*.

It is to be understood that the present invention is not limited to use of the particular preferred strain ATCC 39243 or to organisms fully answering its description. It is especially intended to include other Formula II producing strains or mutants of the described organism which can be produced by conventional means such as x-radiation, ultraviolet radiation, treatment with nitrogen mustards, phage exposure and the like.

In practicing the present process, a rebeccamycin producing strain of *Saccharothrix aerocolonigenes* having the identifying characteristics of strain C38,383 TM RK2 (ATCC 39243), or a mutant or variant thereof is cultivated in an aqueous nutrient medium containing bromide ion and preferably no addition of chloride ion to the medium but still able to support the growth of the organism. The organism is grown in a nutrient medium containing known nutritional sources for actinomycetes. Thus, the organism is grown in a nutrient medium containing an assimilable carbon source such as sucrose, lactose, glucose, rhamnose, fructose, glycerol or soluble starch. The medium should also contain an assimilable nitrogen source such as fishmeal, peptone, peanut meal, cottonseed meal, corn steep liquor, amino acids or ammonium salts. Nutrient inorganic salts can also be incorporated in the medium so as to provide sodium, potassium, ammonium, calcium, phosphate, sulfate, nitrate, carbonate and like ions. Trace elements such as copper, manganese, iron, zinc, etc. are added to the medium if desired, or they may be present as impurities of other constituents of the media. For optimal production of the compound of Formula II, the medium is supplemented with bromide ion and the chloride ion is kept to a minimal level so not to affect the growth of the organism. Submerged aerobic conditions are preferably employed for the production of large quantities of antibiotic, although for production of limited amounts, surface cultures and bottles may also be used. The general procedures used for the cultivation of other actinomycete are applicable to the present invention.

Production of the antibiotic of Formula II can be effected by any temperature conductive to satisfactory growth of the producing organism, e.g. 18° C. to 39° C. and is conveniently carried out at a temperature of about 28° C. The fermentation may be carried out in flasks or in laboratory or industrial fermentors of various capacity. When tank fermentation is to be used it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of the antibiotic of the present invention. The medium in which the vegetative inoculum is grown can be the same as, or different from, that utilized in the tank as long as it is capable to support good growth of the producing organism and is supplemented with a source of bromide ion. Further agitation may be provided by a mechanical impeller. Antifoam agents such as lard oil or silicone oil may also be added if needed. Antibiotic production is monitored by high performance liquid chromatography assay or by conventional biological assay. In general, optimum production of the antibiotic of the present invention is achieved after incubation for about 6 days.

Isolation and purification of the so-obtained analog may be carried out by conventional chromatographic procedures.

Physical and Chemical Properties

The compound of Formula II has the following Physical and Chemical Properties:

Description: Bright yellow amorphous solid
Molecular Formula: $C_{27}H_{21}Br_2N_3O_7$
Molecular Weight: 659.292
Mass Spectrum: Kratos MS 25 Mass Spectrometer. FABMS 660 (M+H)+, 483 (m-176, loss of 4-0 methyl glucose).

Ultraviolet Spectrum, Hewlett Packard 8452 A Diode Array Spectrometer. Concentration 0.93 mg/100 ml. MeOH. Neutral, λmax nm (E 1%/1 cm): 290(58), 316(618), 294(366),238(491), 206(402).

Infrared Spectrum: Perkin-Elmer 1800 FTIR Spectrometer. KBr Pellet (cm$^{-1}$): 3348, 3087, 2932, 2888, 1755, 1708, 1577, 1561 1494, 1467, 1412, 1381, 1324, 1271, 1212, 1191, 1141, 1108, 1078, 1050, 955, 902, 801, 789, 759, 739, 729, 704, 656, 632, 587 562, 496.

360 MHz $^1$H-NMR: Bruker Model AM-3000 Spectrometer. Duel carbon-proton probe, 5mm. Solvent d$_6$-DMSO. Observed chemical shifts (ppm): 11.32 (s,1H), 10.49(s,1H), 9.23(d,1H), 9.04(d,1H), 7.83(d,2H), 7.35(t,1H), 7.34(t,1H), 6.98(d,1H), 5.43(br.d,1H), 5.27(br.t,1H), 4.96(br.d,1H), 4.10(dd,1H), 4.03(d,1H), 3.85(m,1H), 3.66(m,1H), 3.59(s,3H), 3.56(m,2H).

90 MHz $^{13}$C-NMR: Bruker Model AM-3000 Spectrometer. Duel carbon-proton probe, 5mm. Solvent d$_6$-DMSO. Observed chemical shifts (ppm): 170.3, 170.1, 139.4, 138.5, 133.2, 29.9, 129.6, 125.4, 124.5, 124.0, 123.0, 122.7, 122.4, 20.6, 119.4, 117.7, 104.1, 83.9, 81.1, 79.8, 77.7, 72.0, 0.7, 60.0.

Solubility: Soluble in DMSO, DMF, THF. Sparingly soluble in acetone.

Thin Layer Chromatography ($R_f$ values) Normal phase (silica gel 60);

THF: 0.75. CHCl$_3$-MeOH (9:1 v/v): 0.15.

Biological Properties

The compound of formula II was tested against the transplanted mouse leukemia P388 to determine in vivo antitumor activity (Table 1). CDF$_1$ mice were implanted intraperitoneally (ip) with 10$^6$ P388 leukemia cells obtained from DBA/2 donor mice bearing this transplantable murine leukemia. The CDF$_1$ leukemic mice were treated ip with either saline (control mice) or doses of the compound of formula II once at the beginning of one day post-tumor inoculation. These animals were observed daily and their deaths recorded. Average body weight changes (from the day of leukemia implant to the day of last treatment) were determined for all groups as a means of reflecting drug toxicity. The incidence of mice alive in each group on day 5 post-tumor implant was recorded as an additional means of assessing drug toxicity. No therapeutic result was considered as meaningful if more than one mouse per treatment group had died by day 5. Each treatment group consisted of 4 mice; control groups contained 10 mice. The number of mice, if any, surviving to day 30 (the last day of the experiment) was also recorded.

Therapeutic efficacy was evaluated by determining the median survival time (MST) of mice treated with the compound of formula II and comparing it to the MST of parallel control mice. This comparison was made by dividing the MST of the former by the latter and multiplying by 100 to derive a parameter called the percent T/C value. A percent T/C of was considered to represent a meaningful increase in lifespan and hence an active result. As shown in Table 1, the compound of formula II is active against P388 leukemia at dose levels ranging from 16 to 128 mg/kg. The best effect was achieved at a dosage of 64 mg/kg and consisted of a %T/C of 165%. Toxicity was not observed even at the highest dose (128 mg/kg) tested.

TABLE 1

Effect of the compound of formula II on P388 Leukemia$^a$
(Day 1 Treatment)

| Dose, ip. (mg/kg/inj) | Median Survival Times (Days) | % T/C | Average Weight Change (g) | No. of Mice Alive on Day 5 | No. of Mice Alive on Day 30 |
|---|---|---|---|---|---|
| 128 | 15.5 | 155 | 0.6 | 4/4 | 0/4 |
| 64 | 16.5 | 165 | 0.2 | 4/4 | 0/4 |
| 32 | 16.0 | 160 | 0.5 | 4/4 | 0/4 |
| 16 | 14.0 | 140 | 1.3 | 4/4 | 0/4 |
| 8 | 12.0 | 120 | 1.4 | 4/4 | 0/4 |
| 4 | 11.5 | 115 | 1.2 | 4/4 | 0/4 |
| Control | 10 | 100 | 2.1 | 10/10 | 0/10 |

$^a$Mice were implanted with 10$^6$ P388 leukemia cells and treatment with the compound of formula II were begun one day later. Control mice were given saline injections.

The present invention includes within its scope pharmaceutical compositions which comprise an effective tumor-inhibiting amount of the compound of Formula II, or a pharmaceutically acceptable acid addition salt thereof, in combination with an inert pharmaceutically acceptable carrier or diluent.

According to another aspect of the invention, a method is provided for therapeutically treating an animal (preferably mammalian) host effected by a malignant tumor which comprises administering to such host an effective tumor-inhibiting dose of the antibiotic of the compound of Formula II or a pharmaceutically acceptable acid addition salt thereof.

Examples of suitable compositions include solid compositions for oral administration such as tablets, capsules, pills, powders and granules, liquid compositions for oral administration such as solutions, suspensions, syrups and elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the rebeccamycin analog of the present invention will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The present invention is illustrated by the following examples which are not intended to be construed as limiting the scope of the invention.

EXAMPLE 1: General Methods

Solvents and Reagents

Solvents were not redistilled before use. Methanol, acetone, ethyl acetate, isopropyl ether, chloroform, tetrahydrofuran, ethyl ether and hexanes were ACS reagent grade. Water for HPLC refers to in-house deionized water from a Barnstead Nanopure II system. Tetrahydrofuran, methanol and acetonitrile for HPLC use were B and J Brand HPLC grade solvents. Ammonium acetate was Fisher HPLC grade.

Thin Layer Chromatography (tlc)

Normal phase tlc was carried out on Silica gel 60, F-254 plates (EM Reagents, Cat. #5765, 5×10 cm, by 0.25 mm thick). Reversed phase tlc was accomplished with Whatman MKC$_{18}$ plates (Cat. #4803-110, 0.2 mm thick). Plates were developed in Whatman cylindrical jars with caps and 10 ml of eluant. The compound of Formula II was visible as yellow zone in normal lighting or as yellow fluorescing zone with 254 nm or 366 nm ultraviolet light.

Broth Extractions

To whole broths was added Dicalite (speed plus) filter aid. After brief stirring the broths were filtered on large Buchner funnels or on a Tolhurst Centerslung Centrifugal Filter Unit (Model 1B15, Ametek, Inc.). Filtrates were discarded. Mycelial mats were stirred in THF or THF-acetone mixtures for one hour, filtered, and the Dicalite further rinsed with acetone until it no longer fluoresced yellow under UV light. The combined filtrates were concentrated under reduced pressure to yield crude extracts.

Vacuum Liquid Chromatoqraphy (VLC)

A VLC apparatus consists of a Buchner funnel (Kontes, Art. #K-954100) containing a sealed-in sintered glass disc (M porosity), a side hose connection for vacuum and a lower 24/40 joint for attachment of receiving the least polar eluting solvents pulled through under vacuum to form tightly packed 5 cm adsorbent bed heights. Samples were pre-adsorbed onto adsorbent and applied to funnels as slurries, or applied in a solution of the least polar eluting solvent. Step gradients were carried out where predetermined volumes of increasingly polar eluant constituted the fractions. The funnel was sucked dry after each volume of eluant. Fractions were concentrated and combined on the basis of tlc analysis.

Size Exclusion Chromatography

Apparatus consisted of the following: A Glenco column (2.5 I.D. × 100 cm) equipped with solvent resistant teflon end plates; Fluid Metering, Inc. FMI lab pump (Model RP-G150); Glenco glass reservoir (500 ml); Isco Model 328 fraction collector. Columns were slurry packed with Sephadex LH-20 (Pharmacia) preswollen in the eluting solvent. Solvent was delivered in a downward manner through the column at a rate controlled by the lab pump.

Semi-Preparative HPLC

The following components were used to construct an HPLC system: Waters Associates Model 590 Solvent Delivery System pump; Knauer Model 87 Variable Wavelength Detector. Waters Associates Model SR-204 Strip Chart Recorder; Whatman Partisil 10 ODS-3 column (10 mm × 50 cm); 316 stainless steel tubing (0.23 mm i.d.).

Isolation and Purification

Whole broth (40 liters) was filtered with Dicalite and the mycelial mat extracted with THF-acetone (1:2). The combined filtrate yielded 4.9 g crude extract upon evaporation in vacuo. The extract was tirturated with several small volumes of tetrahydrofuran. The THF soluble portion was preadsorbed onto Silica gel H (Merck, 10-40 microns) and chromatographed by a VLC step gradient (isopropyl ether-THF), using a 150 ml funnel containing 50 g silica gel H. The major yellow band eluted with isopropyl ether-THF (1:1). The appropriate fractions were combined and concentrated to yield 370 mg residue. The above material was further fractionated on 50 g Sephadex LH-20 preswollen in THF (bed height 45 cm). Flow rate 1 ml/min. Fractions 17 TM 20 containing the yellow fluorescing band were pooled. Slow addition of hexanes to this volume caused precipitation of a bright yellow solid (90 mg) designated as the compound of Formula II.

EXAMPLE 2: Preparation of cryopreservative culture of *Saccharothrix aerocolonigenes* strain C38,383-RK2 (ATCC 39243).

*Saccharothrix aerocolonigenes* strain C38,383-RK2 was maintained as a cryopreservative culture stored at −80° C. in a Revco ultralow temperature freezer. To prepare a cryopreservative culture, strain C38,383-RK2 was transferred in test tubes on slants of yeast extract-malt extract agar supplemented with $CaCO_3$ which consisted of

| dextrose | 4.0 g |
| yeast extract | 4.0 g |
| malt extract | 10 g |
| $CaCO_3$ | 1.5 g |
| agar | 15 g |
| deionized water q.s. to | 1 liter |

The agar slant was incubated at 28° C. for 7-10 days. The vegetative culture was prepared by transferring the surface growth from the slant culture to a 500 ml Erlenmeyer flask containing 100 ml of a sterile vegetative medium consisting of

| Cerelose | 30 g |
| Pharmamedia (Traders Oil Mill Co.) | 10 g |
| Nutrisoy (Archer Daniels Midland Co.) | 10 g |
| $CaCO_3$ | 3 g |
| deionized water q.s. to | 1 liter |

This vegetative culture was incubated at 28° C. for 48 hours on a rotary shaker set at 250 rev/min. The vegetative culture was mixed with equal volume of cryoprotective solution consisting of

| Sucrose | 100 g |
| Glycerol | 200 g |
| deionized water q.s. to | 1 liter |

Four ml portions of this mixture were transferred to sterile cryogenic tubes (5ml capacity, Corning) and were frozen in a dry ice-acetone bath. The frozen vegetative cultures were then stored at −80° C. in a Revco ultralow temperature freezer.

EXAMPLE 3: Preparation of vegetative culture of *Saccharothrix aerocolonigenes* strain C38,383-RK2 (ATCC 39243)

A vegetative culture was prepared by transferring 4 ml of the cryopreservative culture to a 500 ml Erlenmeyer flask containing 100 ml of a sterile vegetative medium having the same composition as the vegetative medium described in Example 2. The vegetative culture was incubated at 28° C. for 48 hours on a rotary shaker set at 250 rev/min.

EXAMPLE 4: Fermentation in shake flasks

Four mls of the vegetative culture of Example 3 were inoculated into 500 ml Erlenmeyer flasks each containing 100 ml of a production medium consisting of

| Staclipse J-UB Starch (A. E. Staley) | 10 g |
| $KH_2PO_4$ | 2 g |
| magnesium sulfate | 1 g |
| ammonium sulfate | 2.5 g |
| $CaCO_3$ | 2 g |
| KBr | 0.5 g |
| deionized water q.s. to liter | |

The production culture was incubated at 28° C on a rotary shaker set at 250 rev/min. Production of the compound of Formula II was monitored by HPLC. Optimal production of 24-28 μg/ml was generally obtained at 6 days of fermentation.

EXAMPLE 5. Fermentation in tanks

Three hundreds ml of the vegetative culture of Example 3 were mixed with three hundreds ml of production medium (Example 4) in a 2 liter vitro bottle. The mixture was then inoculated into a New Brunswick Microgen fermentor (16 liters nominal volume) containing 10 liters of production medium having the same composition given in Example 4. The fermentation was carried out at 28° C., aeration of one volume per minute and the agitation set at 250 rev/min. The production of the compound of Formula II was monitored by HPLC analysis. The titer of the compound of Formula II reached 5.9–7.1 μg/ml at 5–7 days fermentation.

What is claimed is:

1. The compound having the formula:

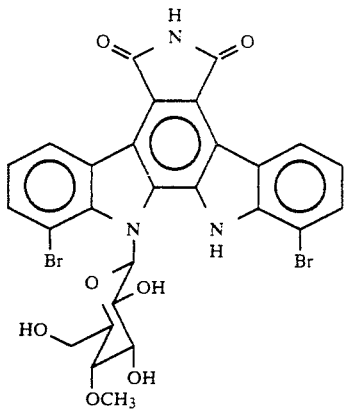

or a pharmaceutically acceptable acid addition salt thereof.

2. A pharmaceutical composition containing an effective antitumor amount of a compound of claim 1 and one or more pharmaceutical carriers.

3. A method for therapeutically treating leukemia P388 tumors in a mammalian host affected by said tumors which comprises administering to said mammalian host an antitumor effective amount of a compound of claim 1.

4. A process for producing the compound of claim 1 which comprises cultivating Saccharothrix aerocolonigenes in a chlorine-deficient, bromine-enriched media, and isolating said compound.

5. The process of claim 4 wherein the rebeccamycin-producing strain is Saccharothrix aerocolonigenes, strain No. C38, 383-RK2 (ATCC 39243).

* * * * *